United States Patent [19]

Chignon et al.

[11] Patent Number: 4,838,251
[45] Date of Patent: Jun. 13, 1989

[54] DYNAMIC KNEE BRACE

[76] Inventors: Jean-Jacques P. Chignon, 15, rue du Jeu de Paume, F 78180 Montigny Le Bretonneux; Jean-Claude Chignon, Résidence Val Fleuri - Bâtiment 34 - rue A. Bickart F, F 77500 Chelles, both of France

[21] Appl. No.: 123,366

[22] Filed: Nov. 20, 1987

[51] Int. Cl.$^4$ .............................................. A61F 3/00
[52] U.S. Cl. .................. 128/80 C; 128/80 F
[58] Field of Search .................. 128/80 C, 83.5, 88, 128/89 R, 80 F, 80 B, 80 A, 80 D, 80 E, 80 G, 80 H; 403/91, 158, 162; 248/558

[56] References Cited

U.S. PATENT DOCUMENTS

| | | | |
|---|---|---|---|
| 911,243 | 2/1909 | Johannesen | 128/80 F |
| 1,656,322 | 1/1928 | Fischer | 128/80 J |
| 2,524,326 | 10/1950 | Murphy | 128/80 C |
| 2,760,774 | 8/1956 | Perez | 128/ |
| 4,050,455 | 9/1977 | Smith | 128/88 |
| 4,245,917 | 1/1981 | Mosciatti | 400/144.3 |
| 4,252,111 | 2/1981 | Chao et al. | 128/80 F |
| 4,289,122 | 9/1981 | Mason | 128/80 E |
| 4,370,977 | 2/1983 | Mauldin et al. | 128/88 |
| 4,492,227 | 1/1985 | Senn et al. | 128/80 C |
| 4,624,246 | 11/1986 | Ajemian | 128/80 C |
| 4,633,867 | 1/1987 | Kausek et al. | 128/88 |

FOREIGN PATENT DOCUMENTS 0583799 1/1978 U.S.S.R. ........................ 128/80 C

Primary Examiner—Edgar S. Burr
Assistant Examiner—Huong Q. Pham
Attorney, Agent, or Firm—Dennison, Meserole, Pollack & Scheiner

[57] ABSTRACT

A knee brace comprises a thigh-piece (1) and a legging (2) capable of pivoting between an extended position and a bent position, together with springs (Pg) stretched over the sides of the brace between anchor elements (10 and 20) fixed to the thigh-piece and the legging in order to urge the thigh-piece and the legging to pivot relative to each other towards at least one of said positions without impeding the movement thereof.

25 Claims, 3 Drawing Sheets

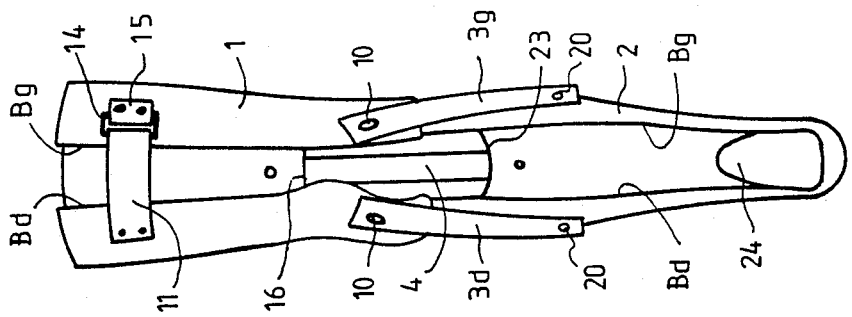
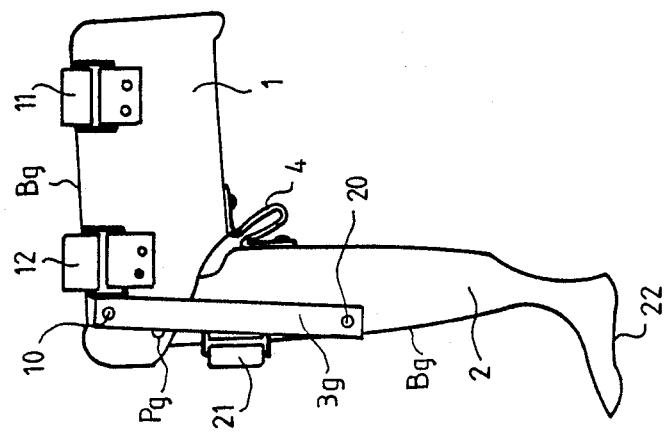
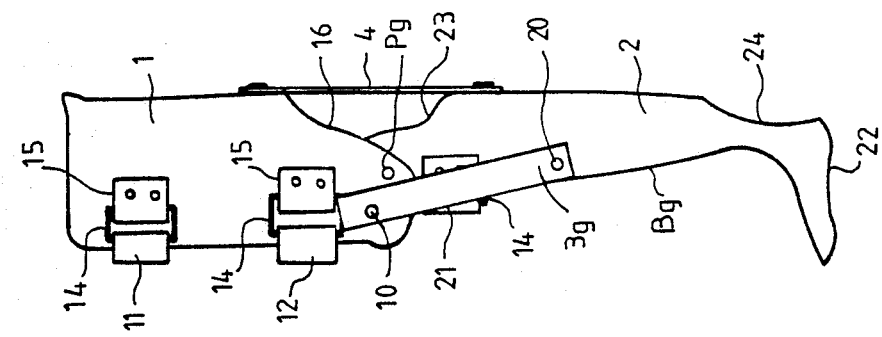

DYNAMIC KNEE BRACE

The invention relates to a knee brace, i.e. to a device which is fixed around the outside of a patient's leg in order to support it, at least on an extended position making it possible to walk.

BACKGROUND OF THE INVENTION

Rigid braces are known which, when put into place, permanently maintain the limb in the extended position. These devices make it possible to stand up to walk, but they do not allow for a normal sitting position.

There also exist hinged braces comprising a thigh-piece and a legging which are hinged together about an axis to allow the knee to bend. In order to provide support in the standing position, such braces include means for maintaining or urging the thigh-piece and the legging into an extended position relative to each other. These means may be constituted by a mechanical latch which, when in operation, prevents bending and which needs to be released before the patient can sit normally. Braces of this type, like those of the rigid type, provide for very stiff walking; and whenever the patient desires to sit down normally, it is necessary to manipulate the brace. Such manipulation requires specially adapted clothing and is difficult for a handicapped person to perform since use is generally also being made of at least one walking stick or crutch.

In other braces, the latch is replaced by resilient return means tending to return the brace to its extended position, and formed, for example, by a splint pressing against the front face of the knee. This arrangement provides for walking which is less stiff, but it is still necessary to perform manipulations in order to achieve a normal sitting position, i.e. the splint must be disconnected, and this gives rise to the same drawbacks as mentioned above.

The invention seeks to avoid these drawbacks of prior knee braces.

Another aim of the invention is to provide a knee brace which allows the leg muscles to work and thus enables the leg to recover its normal functions over a period of time.

SUMMARY OF THE INVENTION

The present invention provides a knee brace comprising a thigh-piece and a legging suitable for partially enveloping the thigh and the lower leg respectively of a patient, said thigh-piece and legging being hinged to each other about an axis to enable the knee to bend between an extended position corresponding to sanding and a bent position corresponding to sitting, the brace further comprising resilient return means suitable for urging the thigh-piece and the legging to pivot relative to each other towards at least one of these positions, and wherein said resilient return means are disposed laterally relative to the thigh-piece and the legging in such a manner as to enable the brace to reach its bent position.

In such a device, relative pivoting between the thigh-piece and the legging is assisted, during walking, by the resilient return means acting in most cases in the extension direction. However, the sitting position can still be reached without it being necessary to manipulate the brace in any way.

In one embodiment of the invention, the resilient return means are constituted by at least one traction spring which is extended between anchor elements fixed to the thigh-piece and to the legging, with the element fixed to the thigh-piece pivoting about the hinge axis relative to the legging, thus simultaneously varying the length of the spring and thus its tension and the magnitude of the force it exerts on the thigh-piece, and the orientation of the spring and thus the lever arm by which said force is applied, with said lever arm being an inverse function of the magnitude of the force.

This spring may be a strip of elastically stretchable cloth.

In accordance with a preferred characteristic, the spring is free to turn relative to each of the anchor elements about respective axes which are substantially parallel to the hinge axis.

Depending on the type of complaint from which the patient is suffering, the spring may exert its effect in one direction only, generally the extension direction, or else in both directions. When operating in both directions, the spring passes over the hinge axis in an intermediate half-bent position and thus tends to move the brace away from this position either towards the extended position or towards the bent position.

The half-bent intermediate position is selected as a function of the nature and the progress of the complaint, and generally corresponds to bending through about 20° from the extended position.

It is preferable for the thigh-piece and the legging to be shaped so as to fit closely to the patient's limb.

BRIEF DESCRIPTION OF THE DRAWINGS

Embodiments of the invention are described by way of example with reference to the accompanying drawings, in which:

FIG. 1 is a side elevation of a brace in accordance with the invention and shown in the extended position;

FIG. 2 is a view similar to FIG. 1, showing the brace in the bent position;

FIG. 3 is a front elevation of the brace in the extended position;

MORE DETAILED DESCRIPTION

The knee brace shown in FIGS. 1 to 3 comprises a thigh-piece 1 and a legging 2 intended to envelop the thigh and the lower leg respectively of a patient. Each of these elements is constituted by a flexible thin sheet (thickness about 3 to 4 millimeters) which is curved to form a channel that opens to the front to allow the limb to be inserted therein. The thigh-piece and the legging are anatomically-shaped, i.e. they are shaped so as to be a close fit around the limb of the patient. They may be conventionally made by thermoforming a sheet of thermoplastic material such as polyethylene around a plaster mold of the limb onto which they are to be fitted, said mold having been previously scraped so as to be exactly the same size as the limb.

In order to improve comfort, a layer of synthetic foam may be put into place on the inside face of the channel while it is being formed.

An important characteristic of the brace in accordance with the invention consists in the sub-condylar fastening of the legging. By fitting closely over the leg of the patient, the top portion of the legging comes into abutment against the condyle, thereby preventing the brace from sliding downwardly and ensuring that the limb is properly held in all positions.

Figure 6:
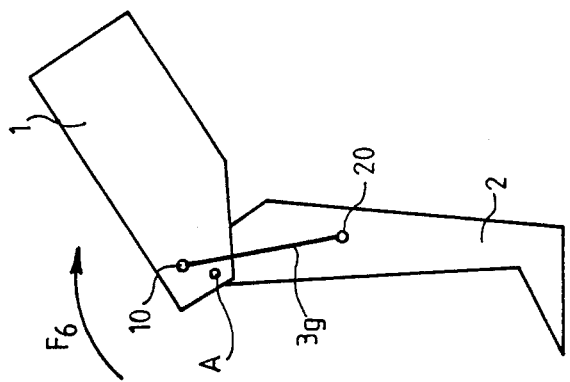
FIGS. 4, 5, and 6 are diagrams showing the brace in positions having respective increasing degrees of bending.
Figure 5:
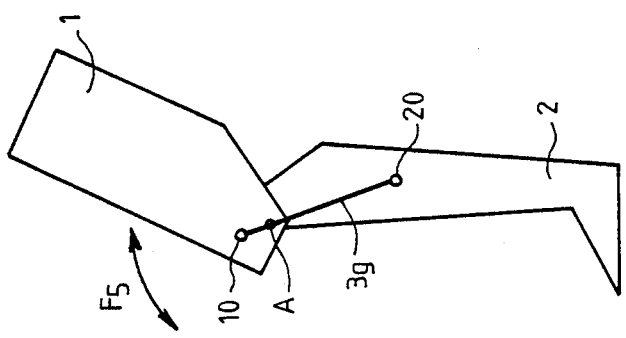
Figure 4:
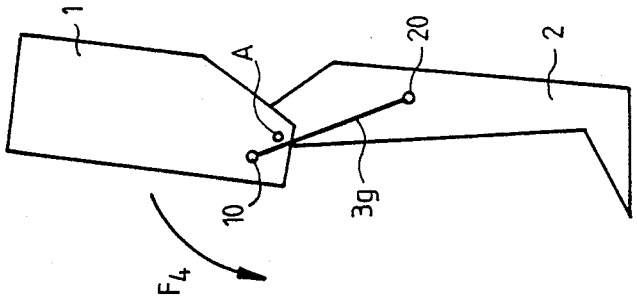

The thigh-piece and the legging are hinged to each other about an axis A represented by a point in FIGS. 4 to 6. This hinge is constituted by two pivots, one of which is referenced Pg in FIG. 1. The pivot Pg comprises two metal parts which are riveted to the left side (the part on the left of the patient's limb) of the thigh-piece and of the legging respectively, said parts rotating relative to each other. The other pivot is mounted coaxially with the first pivot and on the right side of the brace. The precise structure of these metal parts constituting the pivots is not a part of the invention. It is merely indicated that the only metal items which project inwardly, however slightly, from the portion of the brace which is closest to the limb in the region of the joint, in this case the legging, do not rotate relative to the plate from which said portion is made. These projections are rounded and embedded in the foam which lines the plate, and therefore they do not give rise to patient discomfort.

The brace may be secured to the limb by means of straps 11, 12, and 21 which are riveted to one of the edges (in this case the right edge Bd) of the channel formed by the portions 1 and 2, and which are removably fastenable to the opposite edge Bg of the channel. For securing purposes, each strap is passed through a ring 14 which is fixed to a loop 15 of strong cloth which is riveted to the edge Bg. The strap is then folded back and connected to itself for example by mutual fixing strips of the type sold under the trademark Velcro and mounted on facing surfaces of the strap on either side of the ring 14.

The straps 11 and 21 situated respectively at the top of the thigh-piece and at the top of the legging are of constant length once fastened; in contrast, the strap 12 situated at the bottom of the thigh-piece is elastically stretchable in order to enable the thigh-piece to spread sideways in the vicinity of the knee when in the sitting position.

Another strap 4 of fixed length has one end riveted to the rear face of the thigh-piece and has its opposite end riveted to the legging, thereby preventing said parts for going beyond a predetermined extended position. In the bent position this strap is relaxed, but as the brace moves towards the extended position the strap is progressively put under tension. When it is fully under tension, as shown in FIG. 1, the extension movement is stopped The legging 2 includes a portion 22 which goes beneath the patient's foot. This portion is included or omitted depending on the complaint in question.

In addition to the front openings of their channels, the thigh-piece and the legging may respective include a lower rear opening 16 and an upper rear opening 23 for facilitating bending, and the legging may also have a lower rear opening 24 through which the heel of the patient passes.

In accordance with the invention, the traction springs constituted by elastically stretchable strips of cloth 3d and 3g are extended between anchor elements 10 and 20 which are fixed respectively to the thigh-piece and to the legging. Two anchor elements 10 are provided on the thigh-piece respectively on its left side and on its right side, and similarly two anchor elements 20 are provided on opposite sides of the legging, thereby enabling one or more superposed elastic strips 3g to be put into place on each side of the brace. The anchor elements 10 and 20 (whose precise structure does not form part of the invention) may be made of metal and may include: a base which is riveted to the thermoplastic plate from which the thigh-piece or the legging is made; a short rod which is directed outwardly sideways and on which the elastic strips are fitted by means of eyelets provided therein; and a head which screws on to the rod and holds the elastic strips in place. Like the pivots Pg, these anchor elements project only slightly towards the inside and the projecting portions are smoothly rounded and are buried under synthetic foam. In addition, it is advantageous for the base to be riveted to the thigh-piece or the legging at three points, thus enabling the anchor element to be displaced so as to modify the characteristics of the brace, by taking two of the rivets apart and reassembling them after rotating the base about the third rivet.

The elastic return means constituted by the elastic strips 3d and 3g and the anchor elements 10 and 20 are situated entirely on the sides of the brace and leave the front face thereof completely unencumbered. They therefore do not interfere with knee movement.

As can be seen in FIG. 4, when the brace is in a position close to its extended position, the elastic strips 3g (and also the strips 3d) are in front of the hinge axis A. The traction force which they exert on the anchor elements 10 and 20 thus tends to rotate the thigh-piece 1 relative to the legging 2 in the direction of arrow F4 in order to urge the brace into the extended position.

When the brace is in a highly bent position, as shown in FIG. 6, the strips 3g and 3d are behind the hinge axis A. The thigh-piece 1 tends to rotate in the direction of arrow F6 in order to bend even further.

Finally, in a half-bent intermediate position shown in FIG. 5, the anchor elements 10 and 20 are in alignment with the hinge axis A. This solution is therefore unstable and any pivoting therefrom in one direction or the other will be assisted by the elastic strips, as represented by double-headed arrow F5, thereby leading to the situation shown in FIG. 4 or to that shown in FIG. 6.

The length and the tension of the springs 3g and 3d, and thus the force they exert on the anchor elements 10 and 20, are at a maximum in the intermediate FIG. 5 position. However, the springs are still extended when at their minimum length, i.e. in the extension position, so that the movement of the brace is assisted or opposed by the force of the springs throughout its stroke.

As shown in FIGS. 1 and 2, it is desirable for the elements 20 for anchoring the springs on the legging to be very close to the edges Bd and Bg. Preferably, as can also be seen in FIGS. 1 and 2, the hinge axis represented by the pivot Pg is located behind the front plane passing through the anchor elements 20, with the anchor elements 10 being situated in front of said plane in the extended position and behind said plane in the bent position. When passing from one or other of these positions, the elastic strips 3g and 3d rotate freely about the rods of the anchor elements, which are substantially parallel to the hinge axis and over which these strips are threaded, thereby enabling the strips to remain substantially rectilinear. At the same time, the strips slide over the surfaces of the thigh-piece and the legging.

It can be seen in FIG. 2 that the strips 3g (and 3d) extend transversely over the edges Bg and Bd of the channel in the thigh-piece. The traction force which they exert then tends to move these edges apart against the force exerted by the elastic strap 12, thereby opening up the lower portion of the thigh-piece and thus making it possible for the knee to expand sideways, as it does in the sitting position, without inconveniencing the patient. In the extended position, as can be seen in FIG. 1, the orientation of the elastic strip is, in contrast, substantially longitudinal relative to the thigh-piece. Under such conditions, they do not oppose the securing action of the strap 12 which is required to ensure limb stability in the standing position.

The angle between the instability position shown in FIG. 5 and the position of maximum extension shown in FIG. 1 corresponding to standing upright, is commonly about 20° as mentioned above, and it may be determined as a function of requirements by suitable positioning of the anchor elements 10 and 20 on the thigh-piece and on the legging. This angle may also be varied while the brace is in use as function of progress in the complaint, by displacing the anchor elements 10 and/or the anchor elements 20. The return force may also be modulated, in particular by changing the number of elastic strips put into place on either side of the brace. Generally, the return force is reduced by reducing the number of strips as muscle function is re-established.

Another adjustable parameter of the brace is the tension in the strap 12 which provides more or less close coupling between the legging 2 and the patient's lower leg.

Figure 7:
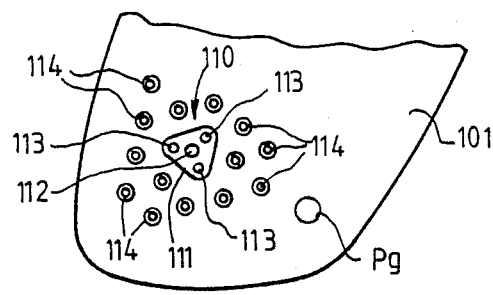
FIG. 7 is a fragmentary view on a larger scale of a variant of the thigh-piece shown in FIGS. 1 to 3.

FIG. 7 is a diagram on a larger scale than FIGS. 1 to 3 showing the bottom end portion of the thigh-piece in a variant brace in accordance with the invention. This thigh-piece 101 includes a left pivot element Pg similar to that of the thigh-piece 1 in FIGS. 1 to 3. It also includes an anchor element 110 for receiving an elastic strip similar to the strip 3g of FIG. 1. As mentioned above, the anchor element 110 comprises a triangular base 111, a rod which is not visible in the figure, and a head 112 screwed onto the rod. As with strip 3g, the elastic strip may include an eyelet to receive the rod with the head 112 holding the strip on the rod. The base 111 is fixed to the thermoplastic plate of the thigh-piece by means of three screws 113 disposed close to the angles of the base 111 and each occupying a vertex of an equilateral triangle. The screws 113 are screwed into tapped metal inserts belonging to a grid of inserts 114 spread over a region of the side surface of the bottom portion of the thigh-piece. The distribution of the inserts is such that three adjacent inserts are disposed at the vertices of an equilateral triangle of side equal to the distance between any pair of screw holes in the base 111. The triangles formed by the grid of inserts are mutually adjacent in this case. These inserts may be fitted in holes drilled through the thickness of the thigh-piece.

A grid of inserts similar to that formed by the inserts 114 may also be provided on the legging of the brace. Such a grid of inserts, whether provided on the thigh-piece or on the legging or on both of them can be used to easily adjust the position of the associated anchor element(s) so as to modify the characteristics of the brace in order to adapt them to the complaint under treatment or to the progress of said complaint over time. Naturally, the positions of the anchor elements situated on the right of the brace may be adjusted in the same way as the positions of the anchor elements situated on the left thereof, but these positions do not need to by symmetrical to each other in all cases.

The inserts 114 may be replaced by seats of a different type, for example by tapped holes provided directly in the material from which the thigh-piece and/or the legging is made if said material has suitable mechanical properties. A grid of seats could also be provided in a pattern different from that described, for example for an anchor element having a number of fixing points other than three, or for which the fixing points are in a different disposition.

Figure 8:
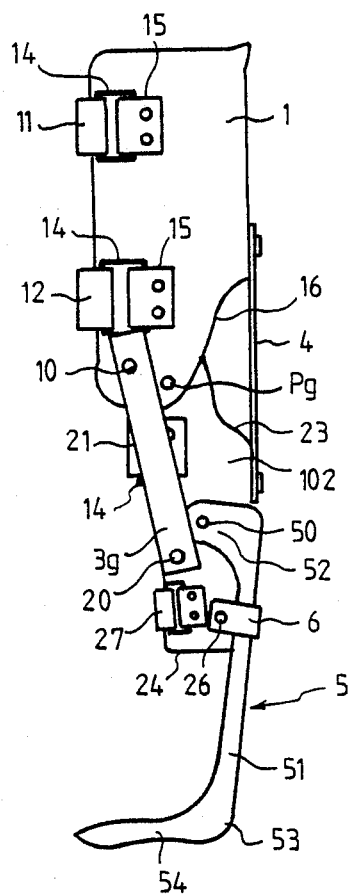
FIG. 8 is a view similar to FIG. 1, showing a variant brace in accordance with the invention.

Reference is now made to FIG. 8, in which items similar to those of FIG. 1 are given the same reference symbols. In the FIG. 8 brace, the thigh-piece 1, the elastic strip 3g, and the strap 4 are identical to the corresponding items in FIG. 1. The top portion of the legging 102 is similar to that of the legging 2 in FIG. 1, however the legging 102 does not extend down to the foot of the patient and it stops at 24 some way from the foot. This brace also includes a foot element 5 which is hinged to the legging 102 about a transverse horizontal axis by means of two pivots 50. The foot element 5 includes a rod 51 which extends along the rear face of the patient's leg when the brace is in place on a limb, and which extends over the bottom portion of the legging with two flaps 52 extending sideways from either side of the top end of the rod 51 in order to cover the sides of the legging above the anchor elements 20, with the flaps 52 carrying the pivots 50.

A resilient member 6, which may be similar to the strip 3g, is extended between anchor elements 26 situated on the sides of the legging 102 beneath the hinged axis of the foot element, and which may themselves be similar to the anchor elements 10 and 20 of the strip 3g. The elastic member 6 passes behind the rod 51 so as to urge the foot element to pivot forwardly.

Figure 9:
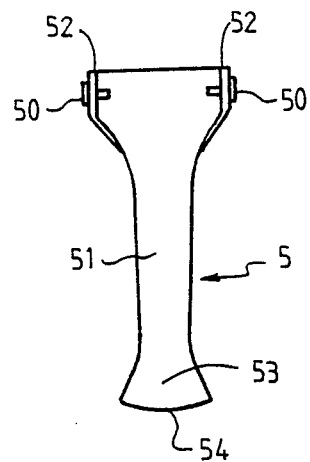
FIG. 9 is a front view of the foot element of the Figure 8 brace.

Each pivot 50 may comprise, as shown in FIG. 9, a head situated on the outside of the flap 52 and a rod passing through the thickness of the flap and penetrating into a blind hole provided in the outer side face of the legging.

The foot element 5 as shown is a foot lifter. Its rod 51 is connected to a portion 53 passing round the heel and a portion 54 extending forwardly beneath the foot of the patient. Depending on circumstances, this foot lifter may be made of rigid or of flexible material. It may also be replaced by a stirrup which does not cover the heel and which is terminated by two bottom end portions covering the sides of the middle of the foot and curving towards each other beneath the foot without actually meeting. In any event, the foot element provides support to the bottom portion of the leg while allowing greater freedom of movement than that which is provided by the FIG. 1 legging 2.

The bottom portion of the legging 102 has a strap 27 similar to the straps 11 and 21 and fixed in the same way as said straps.

We claim:

1. A knee brace comprising a thigh-piece and a legging suitable for partially enveloping the thigh and the lower leg respectively of a patient, and hinged to each other about an axis in order to allow the brace and the patient's knee to bend between and extended position corresponding to standing, a half-bent intermediate position, and a bent position corresponding to sitting, the brace further comprising at least one traction spring suitable for urging the thigh-piece and the legging to pivot relative to each other selectively towards each of said extended and said bent positions, said spring being disposed laterally relative to the thigh-piece and to the legging to enable the brace to reach the bent position, an anchor element fixed to the thigh-piece and an anchor element fixed to the legging, said spring fixed to and extending rectilinearly between said anchor elements, the anchor element fixed to the thigh-piece pivoting, relative to the legging, about the hinge axis and thereby simultaneously varying both the length of the spring, and thus its tension and the magnitude of the force which it exerts on the thigh-piece, and the orientation of the spring relative to the hinge axis to define a lever arm with which said force is applied, with a lever arm being an inverse function of said force, said force exerted on the thigh-piece additionally causing it to spread laterally sideways toward the spring when in the bent position, said spring, in the intermediate position, aligning over the hinge axis, said spring, to each side of the hinge axis toward the extended and bent positions, urging the brace toward the respective extended or bent position and away from the intermediate position.

2. A brace according to claim 1, wherein the spring is a strip of elastically stretchable cloth.

3. A brace according to claim 1, wherein the spring is free to rotate relative to each anchor element about an axis which is substantially parallel to the hinge axis.

4. A brace according to claim 1, wherein said intermediate position corresponds to bending through about 20° from the extended position.

5. A brace according to claim 1, wherein the thigh-piece and the legging are shaped so as to fit closely over the limb of the patient.

6. A brace according to claim 1, wherein the thigh-piece and the legging are made from a flexible thin plate which includes first and second edges and is curved into the form of a channel between the edges which is open to allow the limb to be inserted therein.

7. A brace according to claim 6, wherein straps are provided which are fixed to the first edge and which are releasably attachable to the second edge in order to enable the brace to be secured to the limb.

8. A brace according to claim 7, wherein at least one of the straps is elastically stretchable in order to allow the thigh-piece to spread sideways at the knee in the sitting position.

9. A brace according to claim 1, including means for preventing the thigh-piece and the legging from going beyond a predetermined extended position.

10. A brace according to claim 1, wherein the anchor elements are removably fixed to seats provided on at least one of the thigh-piece and the legging.

11. A brace according to claim 10, wherein the seats are constituted by metal inserts connected to said at least one of the thigh piece and the legging.

12. A brace according to claim 10, wherein a plurality of seats are provided for each anchor element so as to make it easy to adjust the position of the anchor element and consequently to adjust the operating characteristics of the brace.

13. A brace according to claim 10, wherein each anchor element is fixed to a plurality of seats.

14. A brace according to claim 13, wherein said seats are distributed such as patterns of three seats form equilateral triangles, and each anchor element is fixed to three seats of one equilateral triangle.

15. A brace according to claim 1, wherein the legging terminates at a distance above the foot and wherein a foot element extending down to the foot is hinged to the legging about an axis transverse to the foot.

16. A brace according to claim 15, wherein the foot element comes into contact with the rear of the leg and is open towards the front of the leg.

17. A brace according to claim 16, wherein the foot element comprises a rod extending from the legging along the rear of the leg, said rod having a top end portion and two flaps extending from the top end portion of the rod to opposite sides of the legging thereof and above the anchor element of the legging, said flaps being hinged to the legging about a hinge axis.

18. A brace according to claim 17, including an elastic member fixed to opposite sides of the legging and engaged with the foot element beneath the hinge axis of the flaps to urge the foot element forwardly.

19. A brace according to claim 15, wherein the foot element is a foot lifter.

20. A brace according to claim 15, wherein a foot element is a stirrup.

21. A brace according to claim 1, wherein said anchor elements comprise a first pair of anchor elements fixed respectively to the thigh-piece and legging in alignment with each other and laterally to one side of the brace, and a second pair of aligned anchor elements fixed respectively to the thigh-piece an d legging laterally to the opposed side of the brace, said at least one traction spring includes a traction spring extending between each pair of anchor elements, said first and second pairs of anchor elements aligning in planes to the opposite sides of the brace which are unsymmetrical relative to each other.

22. A knee race comprising an upper thigh-piece and a lower legging for partially enveloping the thigh and lower leg respectively of a patient, said thigh-piece being of a channel configuration with opposed longitudinal edges defining a forwardly opening channel mouth for exposure of the forward portion of the thigh partially enveloped by said thigh-piece with said opposed longitudinal edges to opposite sides of the thigh, hinge means joining said thigh-piece and said legging for movement of said thigh-piece between an extended position generally linearly aligned over the legging, and a bent position generally perpendicular to the legging, upper spring anchors fixed to said thigh-piece adjacent each longitudinal edge, tension springs engaged with said anchors and depending therefrom to opposite sides of the channel mouth, and lower spring anchors fixed to said legging, said tension springs engaged with said lower anchors and providing a tension force between the thigh-piece and the legging, said tension springs, in said extended position, exerting a tension force on said thigh-piece longitudinal edges generally parallel to the longitudinal edges, and means for enabling said tension springs, when said thigh piece and said lower legging are in said bent position, exert a tension force on said thigh-piece longitudinal edges generally perpendicular to the longitudinal edges outward of the channel mouth and laterally spread said edges to accommodate the natural tendency for the leg to expand sideways in the bent position thereof.

23. The knee brace of claim 22, wherein each tension spring extends rectilinearly between the associated upper and lower spring anchors and is offset respectively forward of the hinge means towards the channel mouth and rearward of the hinge means away from the channel mouth in the extended and bent positions respectively.

24. The knee brace of claim 23, wherein each tension spring aligns with said hinge means at an intermediate position between said extended position and said bent position.

25. A knee brace comprising an upper thigh-piece and a lower legging for partially enveloping the thigh and lower leg respectively of a patient, said thigh-piece being of a channel configuration with opposed longitudinal edges defining a forwardly opening channel mouth for exposure of the forward portion of the thigh partially enveloped by said thigh-piece with said opposed longitudinal edges to opposite sides of the thigh, hinge means joining said thigh-piece and said legging for movement of said thigh-piece between an extended position generally linearly aligned over the legging, and a bent position generally perpendicular to the legging, upper spring anchors fixed to said thigh-piece adjacent each longitudinal edge, tension springs engaged with said anchors and depending therefrom to opposite sides of the channel mouth, and lower spring anchors fixed to said legging, said tension springs engaged with said lower anchors and providing a tension force between the thigh-piece and the legging, each tension spring extending rectilinearly between the associated upper and lower spring anchors and being offset respectively forward of the hinge means toward the channel mouth and rearward of the hinge means away from the channel mouth in the extended and bent positions respectively, and each tension spring aligning with said hinge means at an intermediate position between said extended position and said bent position whereby movement from said intermediate position to either the extended or bent position provides a biasing force toward the respective position and away from the other position.

* * * * *